United States Patent [19]

Pantridge et al.

[11] 4,090,519
[45] May 23, 1978

[54] DEFIBRILLATORS

[76] Inventors: James Francis Pantridge, Colin House, Dunmurry (Co. Antrim); John Anderson, 38 Ardmore Rd., Holywood (Co. Down), both of Northern Ireland

[21] Appl. No.: 684,885

[22] Filed: May 10, 1976

[51] Int. Cl.² ............................................. A61N 1/36
[52] U.S. Cl. ............................................. 128/419 D
[58] Field of Search ................... 128/419 D, 421, 422, 128/423

[56] References Cited
U.S. PATENT DOCUMENTS 3,605,754  9/1971  Jaros et al. ........................ 128/419 D
3,814,105  6/1974  Howard et al. ................... 128/419 D

OTHER PUBLICATIONS

Machin, "Medical and Biological Engineering", vol. 13, No. 2, Mar., 1975, pp. 240–244.

Primary Examiner—William E. Kamm
Attorney, Agent, or Firm—Holland, Armstrong, Wilkie & Previto

[57] ABSTRACT

A defibrillator which may be portable and which may be used without relying on electrical supply mains. The apparatus comprises a capacitor, an inductance and a pair of electrodes whereby the capacitor is discharged through a patient and the selection of the energy level, the capacitor and the inductance being such that the voltage wave-form of the discharge pulse has a duration of between ten and fifteen milliseconds, a peak value of not more than 4 kilovolts and a minimum rise time to that peak of 1,000 microseconds.

5 Claims, 10 Drawing Figures

DEFIBRILLATORS

DESCRIPTION

This invention relates to a defibrillator, and is particularly although not exclusively concerned with a portable defibrillator, which may be used in the field independently of mains electrical supply.

In the medical field of cardiology there are two main situations of a patient in which defibrillators are of use, these being firstly cardiac arrest, that is to say where the heart has ceased to pump as a result of chaotic electrical activity; and secondly fibrillation, that is to say a condition under which the heart has spasmodically irregular contractions and as a result is not pumping blood efficiently.

The principal requirement of a defibrillator for use in these situations is that it must be capable of causing a controlled electrical shock to the patient, this being achieved by applying special electrodes connected to the device, across the patient's chest.

Known defibrillators for this purpose have embodied means for storing an electrical charge for the shock and have used the so called "Lown" wave form for the electrical output current from the electrodes during the infliction of the shock on a patient, this wave-form being named after the American physician, Bernard Lown, who did much early work on the development of such defibrillators. In such known devices the Lown wave-form peaks at some seven kilovolts and has a duration of some four and a half milliseconds. A further characteristic of wave-forms used previously, has been the very short initial rise time of the wave-form being typically of the order of some 500 microseconds.

Considerable investigation and clinical tests have shown that the output wave-form used with such previous devices has caused high peak currents through the patient during the shock and this has resulted in damage to the myocardium. Further, since a given stored energy was transferred at a high voltage by the device electrical losses in the system were large resulting in considerable inefficiency.

It is an object of the present invention to provide a defibrillator apparatus which alleviates these disadvantages; and particularly, but not exclusively, to provide such a defibrillator which is portable and self-sufficient so that it may be used in the field.

Accordingly, the present invention provides a defibrillator apparatus comprising a capacitor, charging means including a voltage source arranged to charge the capacitor to a given energy level, an inductance, and a pair of electrodes for connection by switching means to said capacitor, one by way of said inductance, whereby the capacitor may be discharged through a patient by means of the electrodes to inflict an electric shock on that patient, the selection of the energy level, the capacitor and the inductance being such that the voltage wave-form, across the electrodes, of the discharge pulse has a duration of between 10 and 16 milliseconds, a peak value of not more than 4 kilovolts and a minimum rise time to that peak of 1000 microseconds when the electrodes are connected across a load resistance of between 50 and 75 ohms. Preferably the minimum rise time is approximately 1100 micro-seconds.

In a preferred embodiment the capacitor has a value of 50 microfarads and the inductance has a valve of 50 millihenries and an ohmic resistance of 18 ohms.

A preferred arrangement of the apparatus comprises a storage battery of cells, an oscillator arranged to be driven from that battery to produce an A.C. voltage output, a rectifier and voltage multiplier circuit connected to that oscillator to produce the voltage for charging said capacitor, and a relay arranged to connect one plate of the capacitor either to said voltage multiplier circuit or to one of said electrodes. Preferably in such arrangement, when said one plate of the capacitor is connected to said one of the electrodes, the voltage multiplier circuit is also connected to that electrode by way of a series resistor. Again in such arrangement, said relay is operable by means of a pair of switches arranged in series and disposed one on each electrode whereby a user of the apparatus can discharge the capacitor when holding the electrodes in place on a patient.

In order to permit a fuller understanding of the above, and other, aspects of the present invention, an embodiment will now be described, by way of example only, with reference to the accompanying drawings in which.

Figure 1:
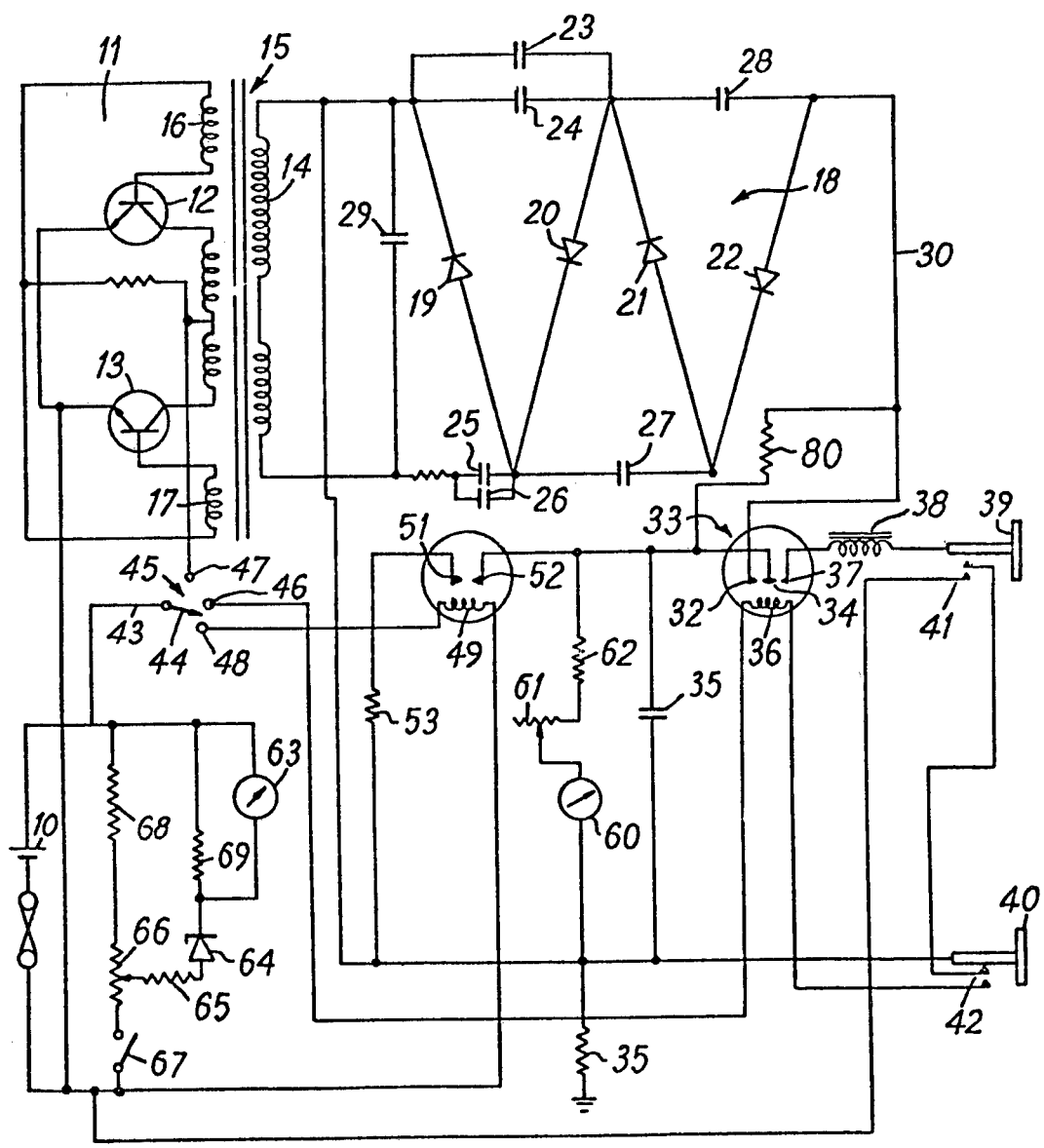
FIG. 1 is a schematic circuit diagram of the defibrillator.

The defibrillator of this embodiment, the electrical circuit of which is shown in FIG. 1, is housed in a suitable portable case (not shown) and arranged to be battery operated. In the circuit it can be seen that electric power is provided by a battery 10, which is a nickel-cadmium rechargable cell battery giving some 20 volts potential.

An oscillator circuit indicated generally at 11, comprising transistors 12 and 13, in this embodiment each 2N 3055, arranged in a push-pull circuit, takes power from the battery 10 to produce an A.C. output which is taken from the oscillator by means of a secondary winding 14 of a toroidal transformer 15 in the output of the oscillator circuit.

Additional windings 16 and 17 of the transformer 15 provide the feed-back elements in the oscillator circuit which operates in a push-pull saturable core mode. The timing of the oscillator is dependent on the rate of core saturation in the transformer and the number of turns in the primary winding. The value of the base bias resistor which is common to two transistors is chosen to ensure the optimum base current needed to achieve a sufficient final drive current in the secondary winding 14 of the transformer, and in this embodiment is 235 ohms. The oscillator operates at 20 KHz, and the transformer ratio is such as to give an output voltage of one kilovolt peak.

The secondary winding 14 is connected across a voltage rectifying and multiplying circuit, generally at 18 which comprises four diodes 19, 20, 21, 22 (MR 996A) with associated charge storage capacitors 23, 24, 25, 26, 27 and 28 (all 0.047 μF) and a smoothing capacitor 29 (0.001 μF) all arranged in known manner to give a rectified output of 4 kilovolts on the live line 30 with respect of the earth line 31.

The output from the voltage multiplying circuit on line 30 is taken to a fixed contact 32 of a relay 33. The movable contact 34 of the relay 33 is connected to one side of a shock energy storage capacitor 35, the other side of which is connected to chassis earth by way of a resistor 85 (one megohm) and to the earth line 31 of the voltage multiplying circuit 18. The movable contact 34 of the relay 33 is normally in contact with the contact 32 when the solenoid 36 of that relay is de-energised.

A further fixed contact 37 of the relay 33 is connected by way of an inductance 38 (50 mH and 18 ohms D.C. resistance) to one 39 of a pair of electrodes 39 and 40, by which the electric shock may be inflicted upon the patient. The other electrode 40 is connected to the earth side of the capacitor 35 and the earth line 31 of the voltage multiplier circuit.

Normally open push button switches 41 and 42 are provided respectively on the electrodes 39 and 40 and arranged so that a user of the apparatus may close the switches when the electrodes are correctly placed across the thoracic region of a patient. The switches 41 and 42 are arranged in series with the solenoid 36 of relay 33 so that closing them can connect it across the battery 10 to energise the relay.

The positive terminal of the battery 10 is connected by way of a line 43 to the movable blade 44 of a three position switch 45 which is resiliently biased to bring the blade 44 into contact with a centre stud 46 of three in the switch. The stud 46 is connected to the solenoid 36 so that with the switch 45 in its normal free position the solenoid 36 can be energised from the battery 10 by switches 41 and 42. A second stud 47 of the switch 45 is connected to the positive line supply of the oscillator 11 so that when movable blade 44 is manually moved to one operating position, that is to say a "charge" position in contact with the stud 47 the oscillator is energised but the relay 36 cannot be operated. A third stud 48 of the switch 45 is connected to the solenoid 49 or a second relay 50 so that when the movable blade 44 is manually moved to a second operating position, that is to say a "reset" position, to contact stud 48 the solenoid of relay 50 is energised.

The relay 50 is provided with a pair of contacts 51 and 52 which are closed when the solenoid 49 is energised, and which are arranged to short out the capacitor 35 by way of a resistor 53 (8 kilohm).

Thus it can be seen that in operation of the device, when the switch 45 is operated to the "charge" position, the oscillator 11 is brought into operation with the result that the capacitor 35 is charged up to a potential of 4 kilovolts, this taking typically some 7 seconds. When the switch 45 is released it returns to engage the stud 46 thus enabling the switches 41 and 42 to be used when the electrodes 39 and 40 are in position on a patient to energise the relay 33 and discharge the capacitor 35 through the inductance 38 and the patient thus inflicting the required electric shock.

If, for any reason, when there is a charge on the capacitor 35 it is required to reset the device for safety or other reasons then the movable blade 44 may be moved to engage the stud 48 at which time the relay 50 is energised thus discharging the capacitor 35 through the protective resistor 53.

A meter 60 is connected in series with a variable resistor 61 (2 megohms maximum value) and a fixed resistor 62 (44 megohms) across the capacitor 35 thus to indicate the charge level on the capacitor 35. The meter 60 is calibrated in terms of the stored electrical energy in the capacitor measured in watt-seconds thus enabling the operator by controlling the charging by switch 45, to exercise control over the energy level of the shock inflicted. A second meter 63 is arranged to be connected in series with a Zener diode 64 (18 volts), a fixed resistor 65 (910 ohms) and a variable portion of a shunt resistor 66 (1 k maximum value) by means of a switch 67, whereby to indicate the charge condition of the battery cells 10 on operation of the switch 67. Additional shunt resistors 68 (2.2 K) and 69 (390 ohms) are provided for additional calibration purposes.

The relays 33 and 50 are of a type in which the contacts are within a gas filled sealed enclosure to enable them to handle the high voltages reliably and without failure. A dummy load resistor (not shown) of some 50 ohms is provided in the cabinet of the device so that the operator may test the working of the device under operating conditions by discharging the capacitor 35 through the dummy load resistor.

In operation of the device, after the relay 33 has been energised to inflict a shock on a patient the capacitor 35 is fully discharged. Consequently, when the relay 36 is de-energised again after the shock and the line 30 from the voltage multiplier is again connected to the capacitor 35, the voltage multiplier instantaneously would effectively see a short circuit in the form of the uncharged capacitor 35. This would result in a high current peak flow from the charged capacitors in the voltage multiplier and this would be reflected back throught the transformer 15 with resultant damage to the transistors 12 and 13.

In order to prevent this occurrence a protective resistor 80 is provided across the line 30 and the live side of the capacitor 35, so that when the relay 33 is energised to discharge the capacitor 35 through the electrode 39 in use, the storage capacitors in the voltage multiplier circuit are also discharged through the protective resistor 80, and via the electrode 39 and the patient. Thus when the line 30 is again connected to the capacitor 35 there is no charge left in the voltage multiplier to cause a transient peak current flow. Since the capacitances of the storage capacitors in the voltage multiplier are small in comparison with that of the capacitor 35, their discharge through resistor 80 does not significantly effect the energy level or nature of the shock to the patient.

Figure 2A:
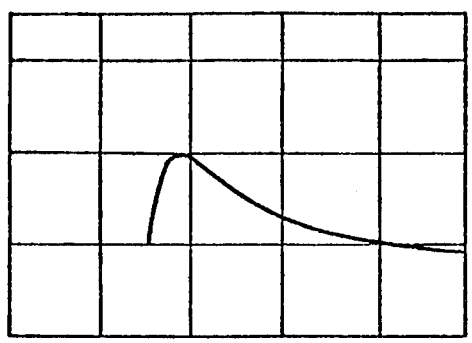
FIGS. 2A, 2B and 2C are typical output current wave-forms produced by the defibrillator of FIG. 1 during different energy transfers.
Figure 2B:
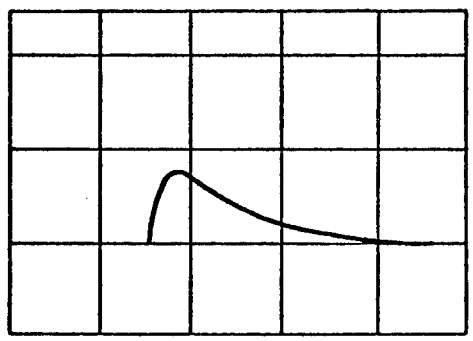
Figure 2C:
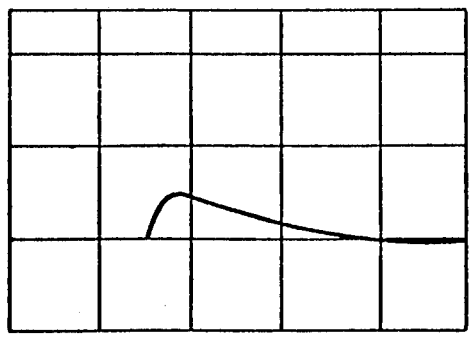

FIGS. 2A, 2B and 2C show, schematically, oscilloscope traces obtained with the above embodiment during the discharge of the apparatus through a 50 ohm load resistance which is typically representative of the average resistance across the thoracic region of a patient. It is to be noted, however, that some estimates would put this resistance at an average of some 75 ohms. The traces represent the voltage drop across a one ohm resistor plotted against time and are therefore indicative of the current flow at any time through the discharge. In each case the horizontal scale is four milliseconds per division and the vertical scale is 40 volts per division, that is to say 40 amps current flow per division. FIG. 2A represents the discharge with the capacitor 36 charged to an energy level of 200 watt-seconds, FIG. 2B represents the discharge with the capacitor 35 charged to an energy level of 100 watt-seconds and FIG. 2C represents the discharge with the capacitor 35 charged to an energy level of 50 watt-seconds.

Figure 3A:
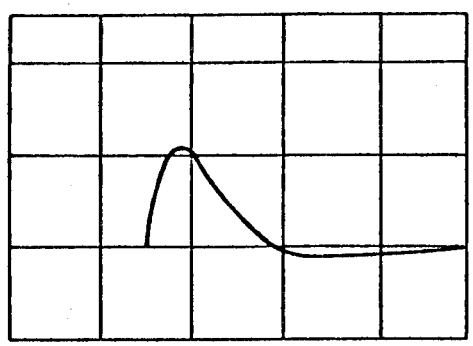
FIGS. 3A, 3B and 3C are similar output current waveforms to those of FIGS. 2A, 2B and 2C, but for a prior art device.
Figure 3B:
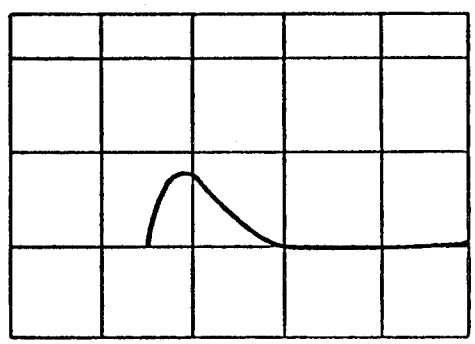
Figure 3C:
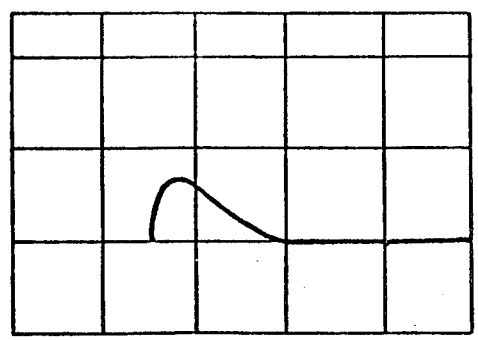
Figure 4A:
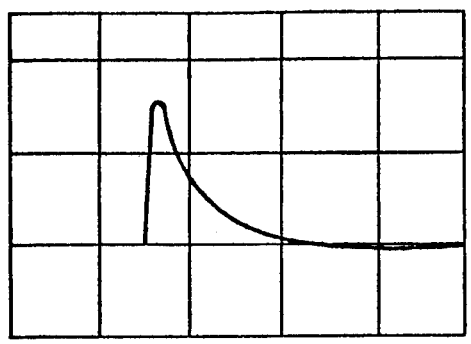
FIGS. 4A, 4B and 4C are similar to FIGS. 3A, B and C but for a further prior art device.
Figure 4B:
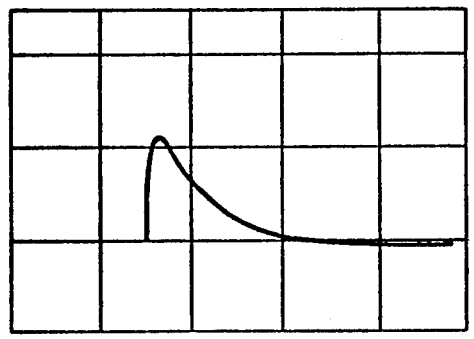
Figure 4C:
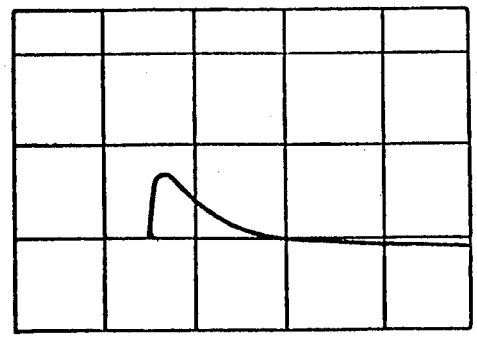

FIGS. 3A, 3B and 3C are traces obtained under exact similar conditions to FIGS. 2A, 2B and 2C, respectively, but for a first prior art apparatus, and FIGS. 4A, 4B and 4C are similar traces obtained under the same conditions, but for a second prior art apparatus.

It is to be noted in the traces of the FIGS. 3A, 3B and 3C and 4A, 4B and 4C that there is a high peak current flow with a very fast initial rise time, in some instances of as little as 500 microseconds. Again, it is to be noted that the current flow duration is short and in fact never exceeds six milliseconds. In contrast to this, in the FIGS. 2A, 2B and 2C relating to the above embodiment of the invention, it can be seen that the rise is substantially increased, being not less than some 1,000 microseconds and being approximately 1,100 microseconds. Again the pulse duration is some 12–14 milliseconds in the traces shown, but can extend to 16 milliseconds.

Research has shown that by keeping the peak current flow down as a result of selecting 4 kilovolts as the maximum potential on the storage capacitor, burning of the myocardium is advantageously reduced from that caused by the high currents of prior art devices. Expanding the rise time has shown advantages in lack of depolarisation in the myocardium.

What we claim is:

1. A defibrillator apparatus comprising a capacitor, charging means including a direct current source arranged to charge the capacitor to a given energy level, an inductance, and a pair of electrodes for connection by switching means to said capacitor, one by way of said inductance, whereby the capacitor may be discharged through a patient by means of the electrodes to inflict an electric shock on that patient, the selection of the energy level, the capacitor and the inductance being such that the voltage wave-form, across the electrodes, of the discharge pulse has a duration of between ten and sixteen milliseconds, a peak value of not more than four kilovolts and a minimum rise time to that peak of one thousand microseconds when the electrodes are connected across a load resistance of between 50 and 75 ohms representative of a patient, said rise time being not less than one thousand one hundred microseconds, said capacitor having a capacitance value of fifty microfarads, said inductance having an inductance value of 50 millihenries and an ohmic resistance value of 18 ohms, said means for charging the capacitor comprising a storage battery of cells, an oscillator arranged to be driven from that battery to produce an A.C. voltage output, a rectifier and voltage multiplier circuit connected to the oscillator to produce the required voltage for charging the capacitor to said energy level and a relay arranged to connect one plate of the capacitor either to said voltage multiplier circuit or to one of said electrodes, and wherein when said one plate of the capacitor is connected to said one of the electrodes, the voltage multiplier circuit is also connected to that electrode by way of a series resistor.

2. Apparatus as claimed in claim 1, wherein said series resistor is shorted across by said relay when said one plate of the capacitor is connected to said voltage multiplier circuit.

3. Apparatus as claimed in claim 2, wherein said relay is operable by means of a pair of switches arranged in series and disposed one on each electrode.

4. A defibrillator apparatus as claimed in claim 3 including an indicating meter arranged to display the state of charge of said capacitor.

5. Apparatus as claimed in claim 1, wherein the switching contacts of said relay are arranged within a sealed gas-filled enclosure.

* * * * *